United States Patent

Mandal

Patent Number: 6,166,272
Date of Patent: Dec. 26, 2000

[54] MOLYBDENUM TRIOXIDE CATALYZED FLUORINATION REACTIONS

[75] Inventor: Sanjay Mandal, Grand Island, N.Y.

[73] Assignee: Occidental Chemical Corporation, Dallas, Tex.

[21] Appl. No.: 09/373,133

[22] Filed: Aug. 12, 1999

[51] Int. Cl.$^7$ .......................... C07C 22/00; C07C 41/00; C07C 209/00

[52] U.S. Cl. .......................... 570/145; 564/412; 568/630; 568/634; 568/639

[58] Field of Search .............................. 570/145; 568/630, 568/634, 639; 564/412

[56] References Cited

U.S. PATENT DOCUMENTS

| | | | |
|---|---|---|---|
| 4,098,832 | 7/1978 | Baxamusa et al. | 570/145 |
| 4,130,594 | 12/1978 | Sendiak | 570/145 |
| 4,183,873 | 1/1980 | Baxamusa et al. | 570/145 |

*Primary Examiner*—Alan Siegel
*Attorney, Agent, or Firm*—Richard D. Fuerle; Anne E. Brookes

[57] ABSTRACT

Disclosed is a method of fluorinating a substrate having the general formula

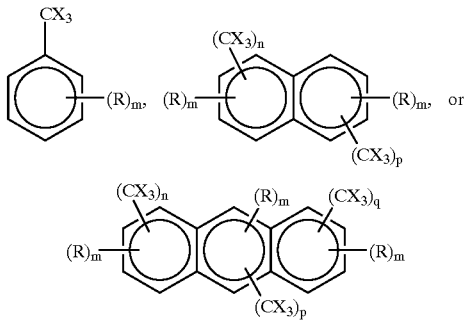

where each R is independently selected from halogen, alkyl from $C_1$ to $C_{12}$, aryl from $C_6$ to $C_{12}$, alkoxide from $C_1$ to $C_{12}$, aryloxide from $C_6$ to $C_{12}$, nitro, amino, alkylamino from $C_1$ to $C_{12}$, and arylamino from $C_6$ to $C_{12}$, each X is independently selected from halogen and at least one X is chlorine or bromine, each m is independently selected from 0 to 5, n is 0 or 1, p is 0 or 1, q is 0 or 1, and n+p+q is 1. The substrate is heated to a temperature of about 40 to about 100° C. and is reacted with a fluorinating agent in the presence of about 0.05 to about 2 wt % molybdenum trioxide. The composition of the substrate, the catalyst, and the fluorinating agent is also disclosed.

12 Claims, No Drawings

MOLYBDENUM TRIOXIDE CATALYZED FLUORINATION REACTIONS

BACKGROUND OF THE INVENTION

This invention relates to the use of molybdenum trioxide as a catalyst for fluorinating certain chlorinated and/or brominated compounds. In particular, it relates to the reaction of benzotrichloride (BTC) or monochlorobenzotrichloride (MCBTC) with hydrogen fluoride (HF) in the presence of a molybdenum trioxide catalyst to make benzotrifluoride (BTF) or monochlorobenzotrifluoride (MCBTF), respectively.

BTF is an important commercial product used, inter alia, as a solvent, a lubricant, and a cleaning solution. It is made by reacting BTC with HF using a molybdenum pentachloride catalyst. See U.S. Pat. No. 4,098,832, herein incorporated by reference, for a detailed description of that reaction. While molybdenum pentachloride is called a "catalyst," it cannot be entirely recovered because it reacts to some extent with air and moisture to form oxyhalides; special precautions are therefore required to preserve it. Moreover, it is soluble in the product and is therefore difficult to separate from the product. It is also very expensive and there is only a single supplier.

SUMMARY OF THE INVENTION

I have discovered that molybdenum trioxide is an effective catalyst for certain fluorination reactions, provided a sufficient concentration is present and the temperature is within a certain range. Unlike molybdenum pentachloride, molybdenum trioxide is a true catalyst and can be recovered and reused after the reaction. In fact, since it is insoluble, it is relatively easy to recover. It is stable in air and moisture, is far less expensive than molybdenum pentachloride, and is available from several suppliers.

DESCRIPTION OF THE PREFERRED EMBODIMENTS

Substrates that can be fluorinated in the process of this invention have the general formula:

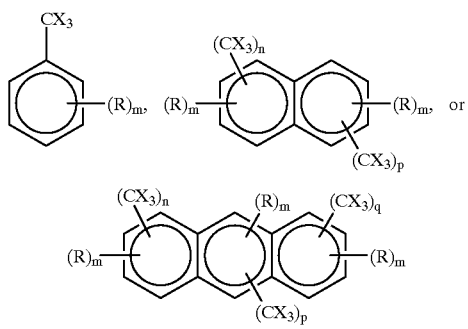

where each R is independently selected from halogen, alkyl from $C_1$ to $C_{12}$, aryl from $C_6$ to $C_{12}$, alkoxide from $C_1$ to $C_{12}$, aryloxide from $C_6$ to $C_{12}$, nitro, amino, alkylamino from $C_1$ to $C_{12}$, and arylamino from $C_6$ to $C_{12}$, each X is independently selected from halogen and at least one X is chlorine or bromine, each m is independently selected from 0 to 5, n is 0 or 1, p is 0 or 1, q is 0 or 1, and n+p+q is 1. Examples of such substrates include BTC, parachlorobenzotrichloride (PCBTC), dichlorobenzotrichloride (DCBTC), p-methylbenzotrichloride, p-nitrobenzotrichloride, p-aminobenzotrichloride, p-phenoxybenzotrichloride, 1-trichloromethyl naphthalene, and 3-trichloromethylanthracene. The preferred substrates are benzotrichlorides (i.e., first formula) and BTF is the preferred benzotrifluoride as it is commercially important.

If the substrate is a liquid, a solvent is preferably not used because a solvent reduces throughput, but a solvent is preferably used to form a solution of a solid substrate. Examples of solvents that may be useful include BTF, PCBTF, and dichlorobenzotrifluoride. Only enough solvent to solubilize the substrate and produce a solution having a workable viscosity should be used.

Examples of fluorinating agents that may be useful in this invention include HF, ammonium fluoride, $NaHF_2$, KF, trimethylamine.HF, pyridinee.10HF, $(NH_4)HF_2$, and $SbF_3$. The preferred fluorinating agent is HF as it is less expensive and easier to use. About 1 to about 1.7 equivalents of a fluorinating agent are used for each chlorine or bromine that one wishes to replace with a fluorine, as less will leave unreacted substrate and more is unnecessary; the preferred amount of fluorinating agent is about 1.1 to about 1.3 equivalents per chlorine or bromine.

I have found that molybdenum trioxide is more effective at temperatures from about 40 to about 100° C. and at concentrations from about 0.05 to about 2 wt %, but at the lower temperatures within that range higher concentrations of the catalyst are required. Thus, there is an inverse relationship between temperature and catalyst concentration. Generally, concentration (in wt %) times temperature (in °C.) should be between about 5 to about 50.

The following examples further illustrated this invention:

EXAMPLE 1

Into a 500 mL polytetrafluoroethylene reactor equipped with, a magnetic stirring bar, a condenser, a thermocouple, a sample port, and an inlet for HF was placed 269.5 g (1.89 mol) of 99% BTC and 0.924 g (0.0064 mol) of $MoO_3$ (0.25 wt % or 0.34 mol % based on BTC). The reactor was heated to about 70° C. while maintaining the condenser temperature at −25° C. using a chiller. The reaction mixture turned blue. With constant stirring, HF gas was introduced to the reactor at an initial rate of 50 cc/min, which was slowly increased to 200 cc/min for the rest of the reaction. The reaction was continuously monitored using gas chromatography (GC). A total of 140.6 g (7.03 mol) of HF was added to the reactor in 13.1 hours. When the reaction was complete, both HF gas flow and heating were turned off. Nitrogen gas was purged through the reactor until all of the HF had been removed, then the reactor was opened to purify and isolate the product. A GC analysis of the final mixture showed 95.6% (GC area) BTF.

EXAMPLE 2

Example 1 was repeated except that the reactor was charged with 264 g (1.35 mol) of 99% BTC and 0.393 g (0.0027 mol) of $MoO_3$ (0.15 wt % or 0.2 mol %, based on BTC). At the 67% level of BTF, it appeared that the reaction rate had slowed, so another 0.263 g (0.0018 mol) of $MoO_3$ (0.10 wt % or 0.13 mol %, based on BTC) was added. A total of 127 g (6.35 mol) of HF was added to the reactor in 13.7 hours. An assay of the reaction mixture by GC showed 97.3% (GC area) BTF.

EXAMPLE 3

Example 1 was repeated except that the reactor was charged with 357.8 g (1.556 mol) of 99.9% PCBTC and 0.90 g (0.0062 mol) of $MoO_3$ (0.25 wt % or 0.4 mol %, based on PCBTC). A total of 109.8 g (5.49 mol) of HF was added to the reactor in 12.1 hours. A GC analysis of the final mixture showed 99.0% (GC area) PCBTF.

EXAMPLE 4

Example 1 was repeated except that the reactor was charged with 300 g (1.31 mol) of 99.9% PCBTC and 0.75 g (0.0052 mol) of $MoO_3$ (0.25 wt % or 0.4 mol %, based on PCBTC), and the reaction was carried out at 55° C. A total of 111 g (5.55 mol) of HF was added to the reactor in 14.5 hours. A GC analysis of the final mixture showed 99.0% (GC area) PCBTF.

EXAMPLE 5

Example 1 was repeated except that the reactor was charged with 425 g (1.85 mol) of 99.9% PCBTC and 0.43 g (0.003 mol) of $MoO_3$ (0.1 wt % or 0.16 mol %, based on PCBTC ), and the reaction was carried out at 55° C. After a total of 159.2 g (7.96 mol) of HF was added to the reactor in 31 hours, the reaction was stopped due to the decrease of the reaction temperature. A GC analysis of the final mixture showed 89.0% (GC area) PCBTF (the rest being underfluorinated products).

I claim:

1. A method of fluorinating a substrate having the general formula

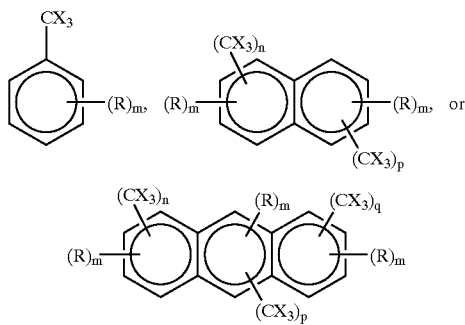

comprising reacting said substrate with a fluorinating agent in the presence of about 0.01 to about 2 wt % molybdenum trioxide at a temperature between about 40 and about 100° C., where each R is independently selected from halogen, alkyl from $C_1$ to $C_{12}$, aryl from $C_6$ to $C_{12}$, alkoxide from $C_6$ to $C_{12}$, aryloxide from $C_6$ to $C_{12}$, nitro, amino, alkylamino from $C_6$ to $C_{12}$, and arylamino from $C_1$ to $C_{12}$, each X is independently selected from halogen and at least one X is chlorine or bromine, each m is independently selected from 0 to 5, n is 0 or 1, p is 0 or 1, q is 0 or 1, and n+p+q is 1.

2. A method according to claim 1 wherein said substrate is a benzotrichioride.

3. A method according to claim 2 wherein said substrate is benzotrichloride.

4. A method according to claim 2 wherein said substrate is monochlorobenzotrichloride.

5. A method according to claim 1 wherein said fluorinating agent is hydrogen fluoride.

6. A method according to claim 1 wherein the concentration of said fluorinating agent is about 1 to about 1.7 equivalents.

7. A method according to claim 1 wherein the concentration of said molybdenum trioxide is about 0.1 to about 0.8 wt %.

8. A method according to claim 1 wherein said substrate is a liquid and no solvent is present.

9. A method according to claim 1 wherein said substrate is a solid and is dissolved in a solvent.

10. A method according to claim 1 wherein said temperature is about 50 to about 80° C.

11. A method according to claim 1 wherein said temperature in ° C. times said concentration in wt % is between about 5 and about 50.

12. A method of preparing benzotrifluoride from benzotrichloride comprising (A) heating said benzotrichloride to a temperature between about 50 and about 80° C;

(B) mixing with said benzotrichloride about 0.1 to about 0.8 wt % molybdenum trioxide; and (C) reacting said benzotrichloride with about 1 about 1.3 equivalents of hydrogen fluoride.

* * * * *